United States Patent
Song et al.

(10) Patent No.: US 10,595,813 B2
(45) Date of Patent: Mar. 24, 2020

(54) METHOD AND APPARATUS FOR MONITORING CARDIAC AND RESPIRATORY CONDITIONS USING ACOUSTIC SOUNDS

(75) Inventors: Zhendong Song, Medina, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1049 days.

(21) Appl. No.: 13/456,346

(22) Filed: Apr. 26, 2012

(65) Prior Publication Data
US 2013/0060149 A1    Mar. 7, 2013

Related U.S. Application Data

(60) Provisional application No. 61/530,129, filed on Sep. 1, 2011.

(51) Int. Cl.
| | | |
|---|---|---|
| A61B 5/02 | (2006.01) | |
| A61B 7/00 | (2006.01) | |
| A61N 1/362 | (2006.01) | |
| A61N 1/365 | (2006.01) | |
| A61B 5/08 | (2006.01) | |
| A61B 5/0205 | (2006.01) | |

(52) U.S. Cl.
CPC ............ *A61B 7/003* (2013.01); *A61N 1/3627* (2013.01); *A61N 1/36514* (2013.01); *A61B 5/02* (2013.01); *A61B 5/0205* (2013.01); *A61B 5/0826* (2013.01)

(58) Field of Classification Search
CPC ................................ A61B 5/02; A61B 5/0205
See application file for complete search history.

(56) References Cited

U.S. PATENT DOCUMENTS

| | | |
|---|---|---|
| 4,546,777 A | 10/1985 | Groch |
| 4,672,977 A | 6/1987 | Kroll |
| 5,165,417 A | 11/1992 | Murphy |
| 5,554,177 A | 9/1996 | Kieval |
| 6,048,319 A | 4/2000 | Hudgins et al. |
| 6,442,433 B1 | 6/2002 | Linberg |
| 6,418,346 B1 | 7/2002 | Nelson |
| 6,480,745 B2 | 11/2002 | Nelson |
| 6,527,729 B1 | 3/2003 | Turcott |

(Continued)

FOREIGN PATENT DOCUMENTS

EP    1391178 A1    2/2004

OTHER PUBLICATIONS

"Phonocardiogram Signal Processing Detection and Boundary Identification of Phonocardiogram Sounds Using an Expert Frequency-Energy Based Metric" by H. Naseri et al., p. 8, 1999.*

(Continued)

*Primary Examiner* — Puya Agahi

(57) ABSTRACT

A medical device system and associated method discriminate respiratory and cardiac conditions using respiratory sounds. A sensing module acquires a first signal and a second signal, at least the second signal acquired from an acoustic transducer. A processor is configured to receive the first signal and to control the sensing module to acquire the second acoustic signal in response to a change in the first signal. The processor discriminates between a cardiac condition and a respiratory condition as a cause of the change in the first signal in response to the second acoustic signal.

22 Claims, 9 Drawing Sheets

(56) References Cited

U.S. PATENT DOCUMENTS

| | | | |
|---|---|---|---|
| 6,599,250 B2 | 7/2003 | Webb | |
| 6,622,045 B2 | 9/2003 | Snell | |
| 6,643,548 B1 | 11/2003 | Mai et al. | |
| 6,869,404 B2 | 3/2005 | Schulhauser | |
| 7,035,684 B2 | 4/2006 | Lee | |
| 7,094,207 B1 | 8/2006 | Koh | |
| 7,139,609 B1 | 11/2006 | Min et al. | |
| 7,424,321 B2 | 9/2008 | Wariar et al. | |
| 7,431,699 B2 | 10/2008 | Siejko et al. | |
| 7,458,939 B2 | 12/2008 | Munk | |
| 7,479,115 B2 | 1/2009 | Savic | |
| 7,736,319 B2 | 6/2010 | Patangay et al. | |
| 7,756,572 B1* | 7/2010 | Fard | A61B 5/0452 600/516 |
| 7,819,814 B2 | 10/2010 | Gavriely et al. | |
| 2002/0072685 A1 | 6/2002 | Rymut | |
| 2004/0254481 A1* | 12/2004 | Brodnick | 600/484 |
| 2005/0222515 A1 | 10/2005 | Polyshchuk et al. | |
| 2006/0020295 A1* | 1/2006 | Brockway et al. | 607/17 |
| 2006/0047213 A1* | 3/2006 | Gavriely | A61B 5/0205 600/513 |
| 2006/0287606 A1 | 12/2006 | Hong et al. | |
| 2008/0009754 A1 | 1/2008 | Chang | |
| 2008/0039730 A1 | 2/2008 | Pu et al. | |
| 2009/0036777 A1 | 2/2009 | Zhang | |
| 2009/0171221 A1 | 7/2009 | Liao et al. | |
| 2010/0094152 A1 | 4/2010 | Semmlow | |
| 2010/0198308 A1* | 8/2010 | Zhou | A61N 1/3601 607/62 |
| 2011/0009746 A1 | 1/2011 | Tran | |
| 2011/0009760 A1 | 1/2011 | Zhang | |
| 2011/0021928 A1* | 1/2011 | Giovangrandi | A61B 5/0205 600/484 |
| 2012/0302898 A1* | 11/2012 | Zhang | A61B 5/0205 600/484 |

OTHER PUBLICATIONS http://www.med.ucla.edu/wilkes/SplitS2main.htm, Mar. 19, 2011.*
http://emedicine.medscape.com/article/157452-treatment, Jul. 28, 2010.*
(PCT/US2012/052985) PCT Notification of Transmittal of the International Search Report and the Written Opinion of the International Searching Authority.

* cited by examiner

METHOD AND APPARATUS FOR MONITORING CARDIAC AND RESPIRATORY CONDITIONS USING ACOUSTIC SOUNDS

RELATED APPLICATION

The present application claims priority and other benefits from U.S. Provisional Patent Application Ser. No. 61/530,129, filed Sep. 1, 2011, entitled "METHODS AND APPARATUS FOR MONITORING CARDIAC AND RESPIRATORY CONDITIONS USING ACOUSTIC SOUNDS", incorporated herein by reference in its entirety.

CROSS-REFERENCE TO RELATED APPLICATIONS

Cross-reference is hereby made to the commonly-assigned related U.S. application Ser. No. 13/456,357, entitled "METHOD AND APPARATUS FOR MONITORING CARDIAC AND RESPIRATORY CONDITIONS USING ACOUSTIC SOUNDS", to Song et al., filed concurrently herewith and incorporated herein by reference in it's entirety.

FIELD OF THE DISCLOSURE

The disclosure relates to medical device apparatus and associated methods for monitoring and discriminating cardiac and respiration conditions based on acoustical signals

BACKGROUND

Numerous implantable and external medical devices are available or have been proposed for monitoring pathological conditions in patients. Various sensors such as electrodes for sensing cardiac electrogram (EGM) or ECG signals, electrodes for measuring thoracic impedance, pressure sensors, and more have been implemented in conjunction with monitoring algorithms employing implantable or external devices for use in diagnosing heart or lung conditions or in managing therapies delivered to treat such conditions. Early intervention and close monitoring is often key to successful therapy management and best outcomes. However, reliable differentiation between respiratory conditions and cardiac conditions is important in guiding and selecting proper treatment. Because some cardiac conditions can cause respiratory changes, and likewise some pulmonary or airway conditions may cause changes in cardiac function such as heart rate, it can be challenging to determine if an underlying cause of a change in respiration is due to a cardiac condition or a respiration system condition. A need remains for a monitoring apparatus and associated methods for detecting and discriminating cardiac and respiratory conditions.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Air flow in the lungs and airways is generated by the pressure gradient produced by the diaphragm as it contracts and relaxes. Air flows through the tracheobronchial tree, into and out of the alveoli in the lungs, causing the respiratory sounds. Respiratory sounds will vary depending on location along the pulmonary anatomy and airways and the presence of pathological conditions. For example, end-inspiratory crackles (sounds heard at the end of a deep breath) are a characteristic of pulmonary edema. The pattern and nature of respiratory sounds or air flow may change over the course of pulmonary edema development. By characterizing respiratory sounds, a prediction of the severity and urgency of possible heart failure decompensation may be made. By integrating respiratory sound monitoring with cardiac monitoring, which could be based on heart sounds, ECG/EGM signals, cardiac impedance and or other technologies, both sensitivity and specificity may both be improved for earlier and effective prediction of heart failure decompensation. Furthermore, the monitoring of respiratory sounds can be used for guiding heart failure therapy as well as for detecting and treating other respiratory conditions, such as apnea or asthma. Acoustic signals collected on or in the thoracic space that may be evaluated for discriminating cardiac and respiratory conditions may include heart sounds, lung sounds, bronchial sounds, tracheal sounds, snoring, coughs and others. Sounds associated with respiration, e.g. lung sounds, bronchial and tracheal sounds, and snoring, are generally referred to herein as "respiratory sounds".

Figure 1:
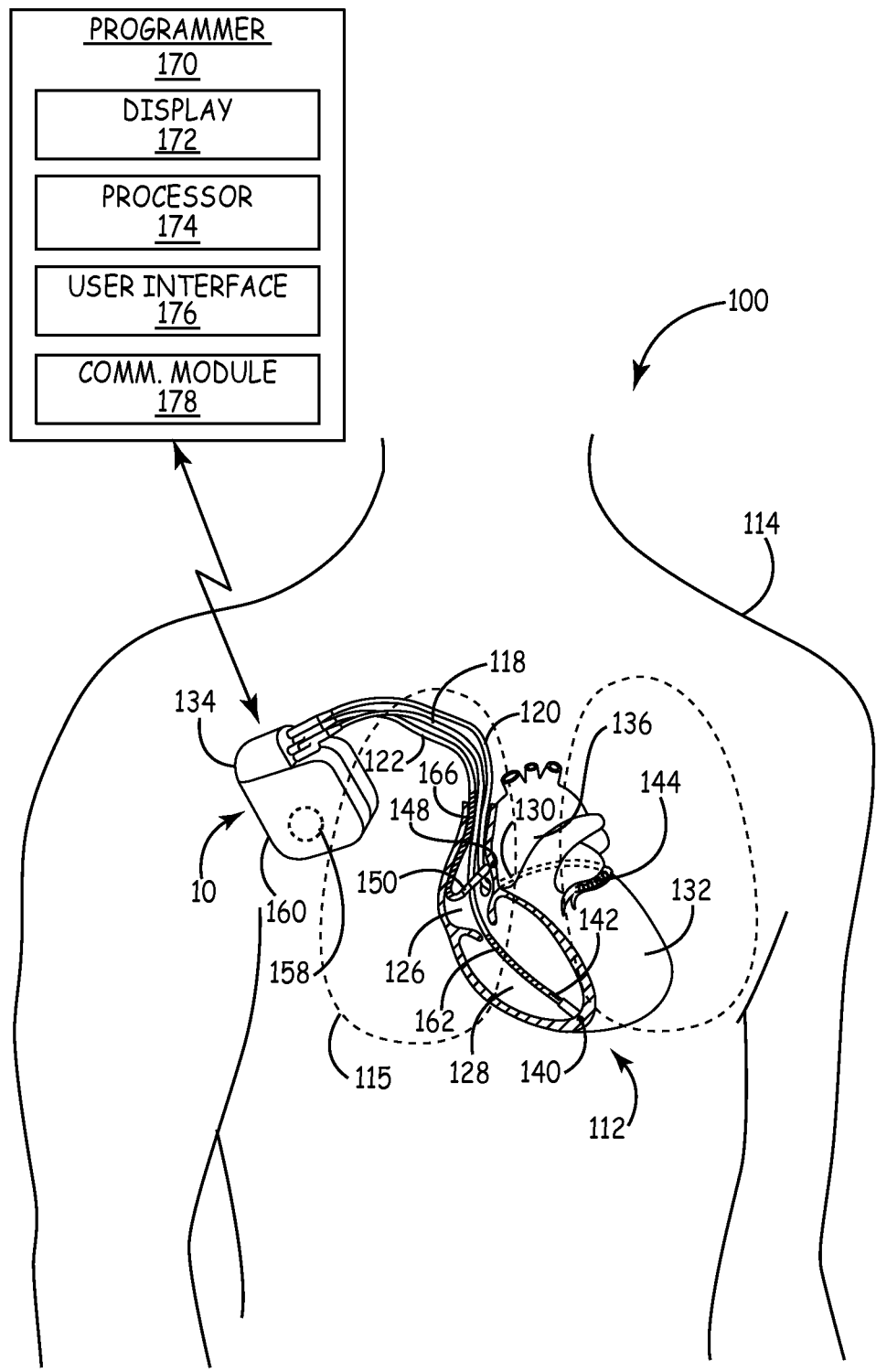
FIG. 1 is a functional block diagram of an implantable medical device (IMD) system for acquiring acoustical signals for monitoring cardiac and respiratory conditions.

FIG. 1 is a functional block diagram of an IMD system 100 for acquiring acoustical signals for monitoring cardiac and respiratory conditions. System 100 includes IMD 10 coupled to leads 118, 120, and 122 which carry multiple electrodes for sensing cardiac EGM signals and/or delivering cardiac pacing pulses. IMD 10 is configured for bidirectional communication with programmer 170. IMD 10 may be, for example, an implantable pacemaker, cardioverter, and/or defibrillator that provides electrical signals to heart 112 via electrodes coupled to one or more of leads 118, 120, and 122.

IMD 10 is shown configured for multi-chamber pacing and sensing in the right atrium (RA) 126, the right ventricle (RV) 128, and the left ventricle (LV) 132 using leads 118, 120 and 122. The system shown is configured for delivering a cardiac resynchronization therapy (CRT) for treating heart failure in patient 114 according to one embodiment. IMD 10 is one example of numerous types of devices that an acoustical signal sensing system and associated methods for monitoring cardiac and respiratory conditions as described herein may be implemented. Such devices may be capable of delivering a therapy such as cardiac pacing, neurostimulation, or fluid delivery for administering a pharmaceutical agent or biological fluid. In other embodiments, an IMD system including acoustical signal monitoring may be provided as a monitoring-only system which acquires and analyzes acoustical signals for diagnostic and prognostic purposes. Furthermore, a device for performing the methods described herein is not limited to fully implantable medical devices but may be implemented using a fully external system including external sensors and signal processors, or a combination of implantable and external devices. As such, the system 100 shown in FIG. 1 is one illustrative embodiment of a system in which the methods described herein may be implemented.

IMD 10 delivers RV pacing pulses and senses RV intracardiac EGM signals using RV tip electrode 140 and ring electrode 142 positioned in the RV 128. RV lead 118 is shown to carry a coil electrode 162 which may be used for delivering high voltage cardioversion or defibrillation shock pulses. IMD 116 senses LV EGM signals and delivers LV pacing pulses using the electrodes 144 carried by multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and deliver LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. While IMD 10 is shown in a right pectoral implant position in FIG. 1, a more typical implant position, particular when IMD 10 is embodied as an ICD, is a left pectoral implant position.

IMD 10 includes internal circuitry for performing the functions attributed to IMD 10 and a housing 160 encloses the internal circuitry. It is recognized that the housing 160 or portions thereof may be configured as an active electrode for use in cardioversion/defibrillation shock delivery or used as an indifferent electrode for unipolar pacing or sensing configurations. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

In the embodiment shown, IMD 10 is also configured for delivering CRT therapy. IMD 10 may be configured to pace in one or both ventricles 128 and 132 for controlling and improving ventricular synchrony. The methods described herein may be implemented in a single, dual or multi-chamber pacemaker or ICD delivering pacing pulses using programmable pacing pulse timing parameters and/or programmable pacing vectors, collectively referred to herein as "therapy control parameters". Therapy control parameters are not limited to timing-related pacing parameters or pacing vector selections and may additionally include any control parameter used by the control processor 16 in controlling the delivery of a therapy by IMD 10.

System 100 includes an acoustical sensor 158, which is shown to be incorporated within housing 160 of IMD 10. Acoustical sensor 158 may be a microphone, accelerometer, e.g. a piezoelectric transducer sensitive to the vibrations caused by motion of the heart structures and air flow into and out of the lungs, or other acoustical sensor. In other embodiments, one or more acoustical sensors may be carried by an intra- or extravascular lead positioned in operative relation to heart 112, the patient's lungs 115, and/or the upper airways (not shown in FIG. 1) for obtaining signals representative of heart and/or respiratory sounds.

IMD 10 may provide acoustical signal data to programmer 170 via wireless telemetry. Acoustical signal data and/or an alarm or alert relating to a detected respiratory or cardiac condition may be transmitted to programmer 170 for display or further transmission to a user via a communication network. Acoustical signal monitoring procedures may be performed automatically by IMD 10 according to a monitoring protocol or upon a user request using programmer 170. A patient or physician alert and/or therapy adjustments may be made automatically by IMD 10 in response to acoustical signal analysis. Alternatively, acoustical signals may be obtained by IMD 10 and transmitted to programmer 170 for analysis and display of results to a user.

Programmer 170 includes a display 172, a processor 174, a user interface 176, and a communication module 178 including wireless telemetry circuitry for communication with IMD 10. In some examples, programmer 170 may be a handheld device or a microprocessor based home monitor or clinical programming device. A user, such as a physician, technician, nurse or other clinician, may interact with programmer 170 to communicate with IMD 10. For example, the user may interact with programmer 170 via user interface 176 to retrieve physiological or diagnostic information from IMD 10. A user may also interact with programmer 170 to program IMD 10, e.g., select values for operational parameters of the IMD. A user interacting with programmer 170 may request IMD 10 to perform an acoustical signal analysis algorithm or request data stored by IMD 10 relating to acoustical signals. Processor 174 receives data from IMD 10 for use in generating a display presented on display 172 including information relating to acoustical data.

Programmer 170 includes a communication module 178 to enable wireless communication with IMD 10. Examples of communication techniques used by system 100 include low frequency or radiofrequency (RF) telemetry, which may be an RF link established via BLUETOOTH®, wireless technology standard, WiFi, or MICS. In some examples, programmer 170 may include a programming head that is placed proximate the IMD 10 to establish and maintain a communication link, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote management of a patient using the acoustical signal monitoring described herein. Remote patient management systems may be configured to utilize the presently disclosed techniques to enable a clinician to review data derived from acoustical signals and authorize programming of IMD pace control parameters. For example, acoustical signals or parameters derived there the signals may be transferred from programmer 170 to a clinic or other expert center for review. The clinician or other expert may then authorize programming of the IMD for delivering or adjusting a therapy via a communications network and programmer 170. Reference is made to commonly-assigned U.S. Pat. No. 6,599,250 (Webb et al.), U.S. Pat. No. 6,442,433 (Linberg et al.) U.S. Pat. No. 6,622,045 (Snell et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming.

Figure 2:
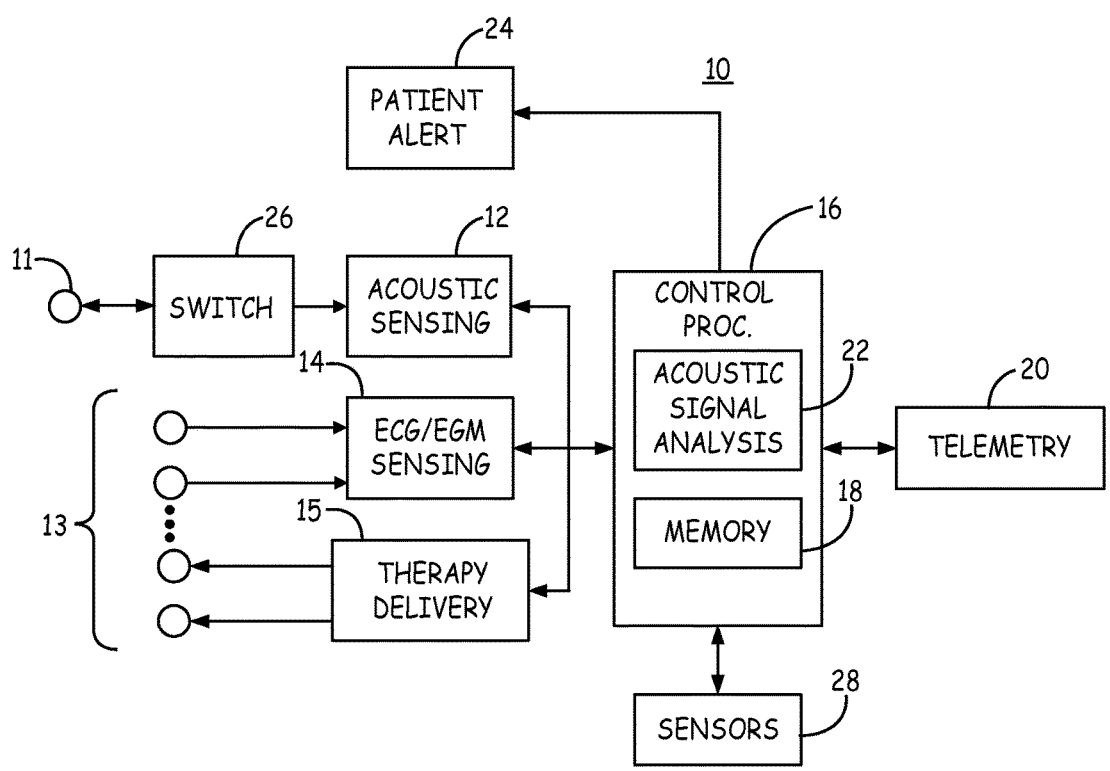
FIG. 2 is a functional block diagram of the IMD shown in FIG. 1.

FIG. 2 is a functional block diagram of IMD 10 shown in FIG. 1. IMD 10 includes an acoustical sensing module 12 coupled to one or more acoustical sensors 11 responsive to respiratory sounds and optionally heart sounds, cardiac signal sensing circuitry 14 and therapy delivery module 15 both coupled to electrodes 13, control processor 16 and associated memory 18, and telemetry circuitry 20. Acoustical sensing module 12 receives signals from acoustical sensors 11 for sensing respiration sounds and optionally heart sounds which are provided to control processor 16 for detecting and discriminating cardiac and respiratory conditions.

Acoustical sensing module 12 is configured to receive analog signals from sensors 11 for sensing one or more respiratory sounds. For example, acoustical sensing module 12 may include one or more "channels" configured to particularly sense specific respiratory sounds based on location, frequency, duration, and/or timing of the respiratory sounds. In addition, ECG/EGM sensing circuitry 14 may be used by control processor 16 to set sensing windows used by acoustical sensing module 12 for sensing heart and/or respiratory sounds. Acoustical sensing module 12 may include one or more sense amplifiers, filters and rectifiers for optimizing a signal-to-noise ratio of acoustical signals. Separate and unique amplification and filtering properties may be provided for sensing respiratory sounds to improve signal quality as needed. In some embodiments, the primary frequencies of the patient's voice may be identified and these frequencies may be filtered by acoustic sensing module 12 or used for noise cancellation during respiratory sound analysis.

In various embodiments, acoustical sensors 11 may be implemented as one or more microphones or 1-, 2- or 3-axis accelerometers, which may be a piezoelectric crystal mounted within an IMD housing or sensor housing, and is responsive to the mechanical motion associated with respiratory and heart sounds. Examples of other embodiments of acoustical sensors that may be adapted for implementation with the techniques of the present disclosure are generally described in U.S. Pat. No. 4,546,777 (Groch, et al.), U.S. Pat. No. 6,869,404 (Schulhauser, et al.), U.S. Pat. No. 5,554,177 (Kieval, et al.), and U.S. Pat. No. 7,035,684 (Lee, et al.), all of which patents are hereby incorporated by reference in their entirety. Practice of the methods and techniques described herein are not limited to a particular type of acoustical sensor.

Switching circuitry 26 may be used to control which acoustical sensor is coupled to sensing module 12 when multiple acoustical sensors are coupled to IMD 10. Acoustical sensors 11 may include one or more implantable and/or external sensors responsive to one or more respiratory sounds (and optionally heart sounds) thereby producing electrical signals correlated in time, amplitude and frequency to the respiratory sounds. The analog signal is processed, which may include digital conversion, by acoustical sensing module 12 to obtain signal parameters, such as amplitude content, frequency content, relative time intervals, or the like as derived by acoustical sensing module 12 or control processor 16. The acoustical sensors 11 and sensing module 12 may be incorporated in an IMD capable of delivering CRT or another cardiac or respiratory therapy or may be implemented in a separate sensing device having wired or wireless communication with IMD 10 or an external programmer or computer.

ECG/EGM sensing circuitry 14, coupled to at least one sensing electrode pair included in electrodes 13, is provided to sense cardiac signals, e.g. P-wave and/or R-wave signals attendant to the depolarization of the atria and ventricles of the heart, respectfully. Sensing circuitry 14 is coupled to electrodes 13, which may include transvenous intracardiac electrodes, epicardial electrodes, or subcutaneous/submuscular electrodes, for sensing cardiac EGM or ECG signals. ECG signals and EGM signals are referred to herein generally as "cardiac electrical signals". Electrodes 13 may correspond to the electrodes 140, 142, 144, 148, 150 162 and 166 shown in FIG. 1 but may include fewer or more electrodes positioned in operative relation to one or more heart chambers. Cardiac electrical signals may be used for timing sensing windows used by acoustical sensing module 12 for obtaining heart sound signals and/or respiration sounds. Cardiac electrical signals may additionally or alternatively be used by control processor 16 for timing electrical stimulation pulses during therapy delivery, e.g. according to programmed pacing intervals, such as a programmed atrial-ventricular (AV) interval and/or inter-ventricular (VV) interval.

Therapy delivery module 15 is provided for delivering pacing pulses to the patient's heart via electrodes 13 using programmable pacing parameters in some embodiments. Electrodes 13 used for delivering pacing pulses may include dedicated pacing electrodes, or may include shared pacing and sensing electrodes. Switching circuitry may be included in therapy delivery module 15 and sensing module 14 for selecting which electrodes 13 are coupled to ECG/EGM sensing circuitry 14 and which electrodes are coupled to therapy delivery module 15 as well as the polarity of such electrodes. While two electrodes are shown coupled to therapy delivery module 15 and two electrodes are shown coupled to ECG/EGM sensing module 14 in FIG. 2, it is recognized that multiple sensing and pacing channels corresponding to multiple heart chambers may require multiple electrodes coupled to each of sensing module 14 and therapy delivery module 15 and such connections may be controlled by a switching circuit, particularly when multipolar electrodes are positioned relative to a single heart chamber.

Therapy delivery module 15 is controlled by control processor 16 to deliver pacing pulses according to a therapy delivery algorithm, such as a programmed CRT therapy, in some embodiments. Control processor 16 receives signals from ECG/EGM sensing circuitry 14 for use in controlling therapy delivery module 15 to deliver appropriately timed pacing pulses. In other embodiments, therapy delivery module 15 may be configured to deliver other electrical stimulation therapies via electrodes 13, which may include stimulation of the upper airways, vagal stimulation, phrenic nerve stimulation or other neurostimulation for treating a detected respiration or cardiac condition. In still other embodiment therapy delivery module may include a fluid pump for delivering a drug for treating a detected condition.

Control processor 16 may include any one or more of a microprocessor, a digital state machine, a digital signal processor (DSP), an application specific integrated circuit (ASIC), a field-programmable gate array (FPGA), or equivalent discrete or integrated logic circuitry. In some examples, processor 16 may include multiple components, such as any combination of one or more microprocessors, one or more controllers, one or more DSPs, one or more ASICs, or one or more FPGAs, as well as other discrete or integrated logic circuitry. The functions attributed to control processor 16 herein may be embodied as software, firmware, hardware or any combination thereof, implemented in a single device or distributed across two or more devices, which may include one or more implantable devices, external devices, or a combination of both.

Control processor 16 includes an acoustical signal analysis module 22 for analyzing respiratory sound signals obtained by sensing module 12 to detect and discriminate respiratory events. The analysis module 22 includes circuitry and/or computer-readable instructions for performing an algorithm for deriving parameters and/or trends or relative changes in parameters derived from the acoustical signals for detecting a respiratory condition.

Memory 18 stores algorithms used by control processor 16 for performing monitoring procedures. Such algorithms may include monitoring protocols for acquiring acoustical signals as well as controlling therapy response and/or triggering alert conditions. Memory 18 may also be used to store other data and information used by control processor 16 for controlling device functions, including a pacing or neurostimulation therapy delivered by therapy delivery module 15, controlling sensing functions by ECG/EGM sensing circuitry 14, controlling telemetry module 20, and controlling patient alert 24 in response to detecting an alert condition based on acoustical signals and cardiac signals.

Memory 18 may include computer-readable instructions that, when executed by processor 16, cause IMD 10 and processor 16 to perform various functions attributed throughout this disclosure to IMD 10 and processor 16. The computer-readable instructions may be encoded within memory 18. Memory 18 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

It is contemplated that IMD 10 may include or be coupled to other sensors 28 which provide signals to control processor 16 correlated to other physiological conditions of the patient. Sensors 28 may include an activity sensor, posture sensor, pressure sensor, oxygen sensor, temperature sensor, impedance sensor or the like. Sensor signals may be used by control processor 16 in detecting a physiological condition of the patient indicating a need to provide or adjust therapy or generate a patient alert. In some embodiments, sensors 28 are used to sense additional cardiac signals for use in detecting and discriminating cardiac and respiratory conditions. Other sensor signals may be used in combination with acoustical signals to confirm a change in a monitored acoustical signal and/or for triggering the monitoring and analysis of acoustical signals for detecting a condition.

Telemetry module 20 is configured for bidirectional communication with an external programmer or computer operating software for programming the IMD 10. Control processor 16 may generate acoustical data and information relating to a monitored condition that is transmitted to an external device via telemetry module 20 for review by a clinician. In some embodiments, functions attributed herein to control processor 16 may be performed across one or more processors that may include an external processor receiving data from telemetry module 20.

Figure 3:
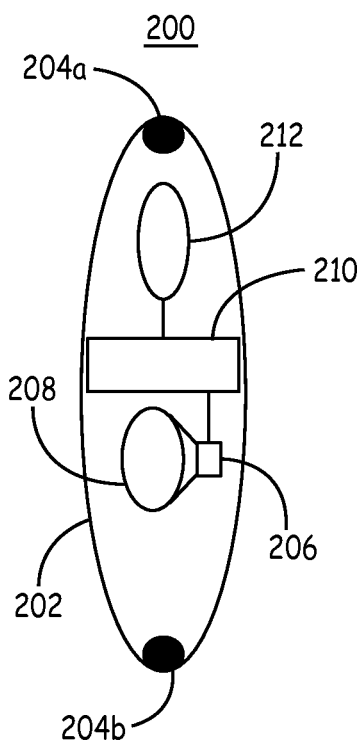
FIG. 3 is a schematic diagram of a monitoring device which may be used in a medical device system for monitoring acoustical signals.

FIG. 3 is a schematic diagram of a monitoring device 200 which may be used in a system for monitoring acoustical signals. Device 200 is provided as an external monitoring device having an adhesive patch substrate 202 for attaching to a patient's skin at a desired monitoring location. Device 200 includes hybrid circuitry and components for providing the described monitoring functionality including electrodes 204a and 204b, an acoustic transducer 206, signal processing circuitry 208, microprocessor and communication circuitry 210 and other sensor modules 212.

Electrodes 204a and 204b may be used for acquiring ECG signals and may be useful for measuring thoracic impedance signals. Acoustic transducer 206 generates an analog signal responsive to respiratory and cardiac sounds. Signal processing circuitry 208 receives the analog signal and performs signal conditioning, which may include amplification, filtering, rectifying, digitizing the analog signal, ensemble averaging or other signal processing steps. Signal processing circuitry 208 alone or in combination with microprocessor and communication module 201 may further derive respiratory sound parameters from the conditioned signal. Heart sound-related parameters may additionally be derived from the acoustical signals for use in detecting cardiac and respiratory conditions.

Microprocessor and communication circuitry 210 may be communicatively coupled to a programmer or computer for wireless or wired communication. Microprocessor and communication circuitry 210 transmits acoustical data to a programmer or computer, which may be receiving acoustical data from multiple monitoring devices 200 positioned at different locations with respect to the patient's respiration system and heart. The external programmer or computer may further process and analyze the acoustical data and display the data to a clinician. The data may be annotated to indicate any detected conditions or events and include a display of historical data to enable a clinician to view trends or changes in a patient's condition.

In other embodiments, the components shown in device 200 and the described functionality may be implemented in an implantable sensing device which may be a wireless or lead-based sensor positioned deployed to a desired monitoring location within the patient body, either intra- or extra-thoracically. Device 200 may be configured for telemetric communication with an IMD, such as IMD 10 shown in FIG. 1, to provide acoustical data for use in cardiac and respiratory condition detection and therapy control.

Figure 4:
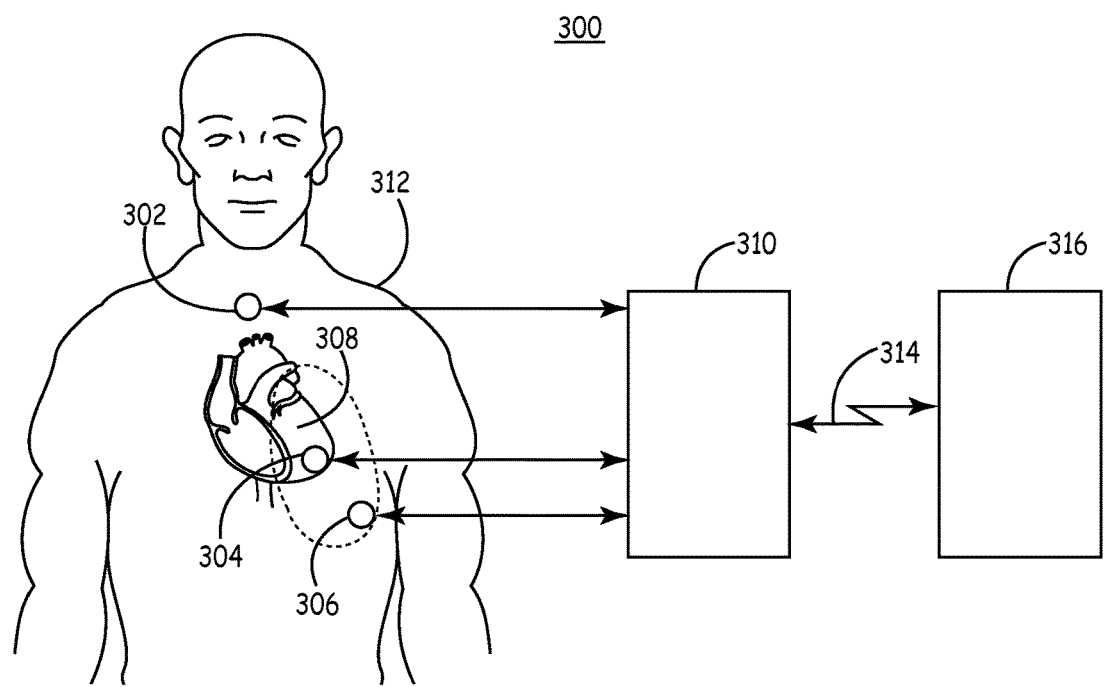
FIG. 4 is a schematic diagram of an acoustical signal monitoring system according to one embodiment.

FIG. 4 is a schematic diagram of a monitoring system 300 according to one embodiment. System 300 includes multiple sensors 302, 304 and 306 positioned on patient 312 along thoracic locations that allow acoustical signals to be obtained at different levels of the tracheobronchial tree and lungs. Sensors 302, 304 and 306 may correspond to the monitoring devices 200 shown in FIG. 3 which include electrodes and optionally other physiological sensors in addition to an acoustic transducer. Alternatively, sensors 302, 304 and 306 may include only acoustic transducers and associated circuitry for acquiring acoustic signals, and separate electrodes and/or other sensors may be placed on patient 312 for acquiring ECG signals and/or other physiological signals. In other embodiments, one of sensors 302, 304 and 306 may correspond to a monitoring device 200 that includes ECG electrodes and optionally other physiological sensors, and the others of sensors 302, 304 and 306 may include only acoustical signal monitoring.

While three sensors 302, 304 and 306 are shown positioned on patient 312, it is contemplated that one or more sensors may be positioned in one or more positions along a mediolateral axis, one or more positions along a craniocaudal axis (i.e. superior-to-inferior), and/or one or more positions along dorsoventral locations. In particular, two or more craniocaudal positions may be desirable to obtain acoustical signals at different levels along the tracheobronchial tree and lungs.

As shown in FIG. 4, one sensor 302 is positioned superiorly, at the level of the trachea or bronchioles for sensing respiratory sounds. Another sensor 304 is positioned relatively inferiorly to sensor 302, at a level of the patient's heart 308, for sensing heart sounds. Sensor 304 may additionally be used for sensing respiratory sounds in the lungs. A third sensor 306 is positioned further inferiorly and laterally, for sensing respiratory sounds in the alveoli, at an inferior level with respect to sensor 304. These varying positions, as described further below, allow respiratory sounds and optionally heart sounds to be monitored for detecting and discriminating cardiac and respiratory conditions based on changes of the respiratory sounds at particular anatomical locations. Respiratory sound signatures may be established which allow different respiratory conditions to be detected. These respiratory sound signatures include particular changes in respiratory sounds at particular anatomical positions that signify a particular cardiac or respiratory condition.

Sensors 302, 304 and 306 transmit acoustic signals to an external device 310, which may be a home monitor, programmer, or other external device configured to communicate with sensors 302, 304 and 306 via wireless telemetry or hardwired communication. External device 310 may be coupled to a communication network that enables data corresponding to respiratory sound signals acquired by sensors 302, 304 and 306 to be transmitted to a remote device 316, which may be a clinican's computer, a centralized database, cell phone, or other networked device. A clinician may then review respiratory sound data and respiratory and cardiac events or conditions detected based on the respiratory sound data.

Respiratory sounds may be characterized according to the anatomical location the sound is produced. For example, respiratory sounds at the tracheal, bronchial, bronchovesicular, and vesicular (alveoli) levels may be differentiated by frequency, amplitude and inspiration and expiration duration characteristics. The tracheal sound can be sensed using a sensor placed near or over the trachea. In a normal patient, the tracheal sound is generally highest in amplitude of the respiratory sounds and is high in frequency. The inspiratory sound duration is approximately equal to the expiratory sound duration.

The bronchial sound can be sensed using an acoustical sensor placed over the manubrium of the sternum, or implanted at approximately that level, and is high in amplitude and frequency. The expiratory sound may be louder than the inspiratory sound. The bronchovesicular sound, which can be sensed at approximately the level of the first or second intercostal space anteriorly or between the scapula posteriorly, is intermediate in amplitude and frequency and the inspiratory and expiratory sound durations are approximately equal. Vesicular sounds, corresponding to airflow in the alveoli, can be sensed generally anywhere over the lungs and are low amplitude, low frequency sounds. The inspiratory sound duration is approximately equal to the expiratory sound duration. Sensors placed lowest (inferiorly) along the thorax along any mediolateral or anteroposterior location may be used to sense vesicular sounds.

As such, two or more sensors may be placed at different locations, particularly spaced apart craniocaudally at different levels along the tracheobronchial tree and lungs, to enable sensing of different respiratory sounds. Once baseline respiratory sound parameters derived from an acoustical signal sensed at a particular location are established, changes in these parameters over time may be used to detect cardiac or respiratory conditions. Furthermore, location-dependent changes in respiratory sounds may be used to discriminate between conditions.

Sensor 304 is indicated as used for acquiring acoustical signals corresponding to heart sounds. Clinicians typically refer to four heart sounds, S1, S2, S3 and S4. The first heart sound, S1, corresponds to the start of ventricular systole and is generated by the abrupt closure of the mitral and tricuspid valves between the ventricles and atria as ventricular pressure exceeds atrial pressure. S1 generally has a duration of about 150 ms and a frequency on the order of 20 to 250 Hz. The second heart sound, S2, is generated by the closure of the aortic and pulmonary valves, near the end of ventricular systole and start of ventricular diastole. S2 is therefore correlated to diastolic pressure in the aorta and the pulmonary artery. S2 generally has a duration of about 120 ms and a frequency on the order of 25 to 350 Hz.

The third heart sound, S3, is associated with early, passive diastolic filling of the ventricles, and the fourth heart sound, S4, is associated with late, active filling of the ventricles due to atrial contraction. The third sound is generally difficult to hear in a normal patient using a stethoscope, and the fourth sound is generally not heard in a normal patient. Presence of the third and fourth heart sounds may indicate a pathological condition.

Figure 5:
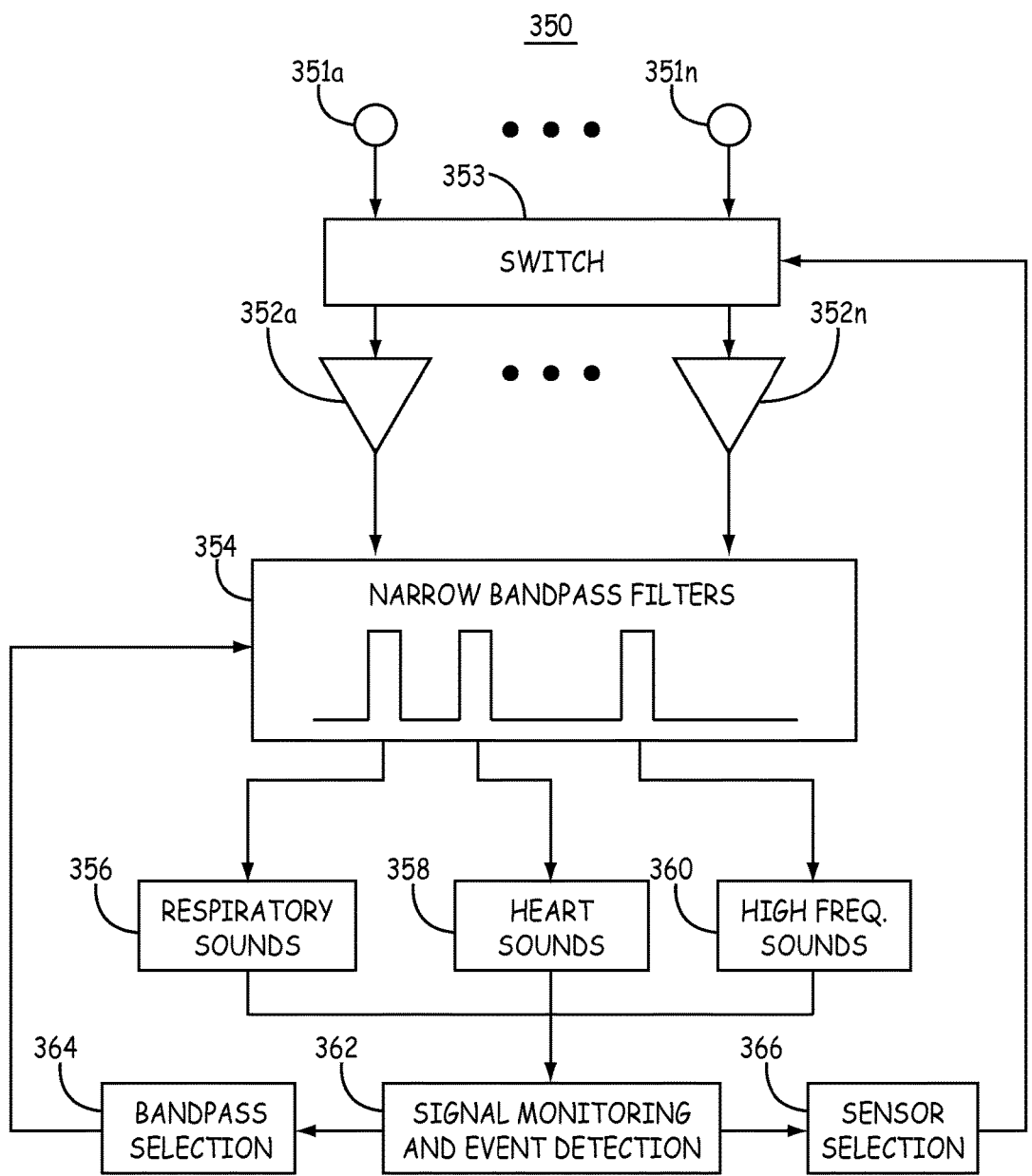
FIG. 5 is a functional block diagram of an acoustic sensing module according to one embodiment.

FIG. 5 is a functional block diagram 350 of an acoustic sensing module according to one embodiment. Acoustic sensors 351a through 351n are coupled to switch 353, which may be used for selecting which sensors 351a through 351n are coupled to sense amplifiers 352a through 352n. Multiple sense amplifiers 352a through 352n may be provided to allow multiple acoustic signals to be acquired simultaneously. Alternatively, one or more sense amplifiers are selectively coupled to sensors 351a through 351n one at a time to allow sequential signal acquisition from more than one sensor.

In some embodiments, sense amplifiers 352a through 352n may include wide bandpass or low pass filtering. The wide bandpass or low pass filtering filters high frequency signals that are considered to be non-physiological. For example a high cut-off frequency may be approximately 1 kHz to eliminate or reduce high frequency noise such as electromagnetic interference. If a wide bandpass filter is used, a low cutoff frequency may be approximately 0.1 Hz to pass signal frequencies typical of respiratory and heart sounds. A low cutoff frequency may be used to eliminate or reduce low frequency noise associated, for example, with patient movement.

The acoustical signals are then filtered by selected narrow bandpass filters 354. Filtering of acoustical signals may be implemented in one filter with different passbands or a cascade of multiple filters to provide separate output signals corresponding to respiratory sounds 356, heart sounds 358 and other characteristic higher frequency sounds 360, such as high frequency "crackles" or wheezing, typically associated with a pathological condition such as lung edema due to congestive heart failure, asthma, or other conditions that result in abnormal high frequency respiratory sounds. As such, higher frequency sounds 360 may still be considered respiratory sounds but are characteristic of pathological conditions and normally not present in respiration sounds.

While three narrow bandpass filters are suggested in FIG. 5 for separating each of respiratory sounds 356, heart sounds 358 and high frequency sounds 360, it is contemplated that additional narrow bandpass filters may be used. For example, two or more narrow bandpass filters may be used to separately obtain respiratory signals corresponding to different anatomical locations, e.g. higher or lower along the tracheobronchial tree and lungs. Two or more narrow bandpass filters may be used to separately obtain heart sounds corresponding to different sounds during the cardiac cycle, i.e. S1, S2, S3 and S4. Narrow bandpass filters will have a bandwidth necessary to pass a signal of interest. For example a "narrow" bandpass filter used for obtaining a particular respiration or heart sound may have a bandwidth of anywhere between approximately 5 Hz and 400 Hz to obtain sounds associated with crackles, rales, wheezes or other pathological sounds as well as normal sounds of inspiration and expiration. In some embodiments, a notch filter may be included to remove voice sounds or other unwanted sounds.

As such, respiratory and heart sounds may be acquired simultaneously from a single sensor and separated by narrow bandpass filtering of the acoustical signal around a characteristic frequency of a given respiratory or heart sound. Signal monitoring and event detection 362 performs algorithms for deriving parameters from the signals corresponding to respiratory sounds 356, heart sounds 358 and/or high frequency pathological sounds 360 for controlling bandpass selection 364, sensor selection 366 and for detecting respiratory or cardiac conditions based on the signal analysis.

Bandpass selection module 364 is controlled by signal monitoring and event detection module 362 for selecting which filters 354 are applied to the outputs of sense amplifiers 352a through 352n. In an illustrative example, heart sound signals may be monitored continuously or periodically by selecting a narrow bandpass filter 354 that provides a good signal-to-noise ratio of a monitored heart sound. If a change in the heart sound is detected, respiratory sound monitoring may be triggered. For example, if a change in the amplitude or other aspect of the S1 or S2 heart sound is detected by signal monitoring and event detection 362, bandpass selection 364 may be controlled to cause narrow bandpass filters 354 to apply a different narrow bandpass filter to an acoustical signal to obtain respiratory sounds 356. Respiratory sounds 356 are then monitored, which may be in addition to continued monitoring of heart sounds 358, to determine if a respiratory or cardiac condition exists that warrants a patient or physician alert or adjustment to a therapy.

Additionally or alternatively, monitoring of high frequency sounds 360 may be triggered based on an analysis of heart sounds 358 or respiratory sounds 356 for detecting a condition. In other embodiments, respiratory sounds 356 may be monitored continuously or periodically and trigger acquisition of heart sounds 358 through selection of a narrow bandpass filter 354 when a condition is detected or suspected based on respiratory sound analysis.

In addition or alternatively to controlling narrow bandpass filter selection in response to signal monitoring, acoustical sensor selection 366 may be controlled based on signal monitoring. For example, when multiple sensors are deployed to different anatomical locations, signal monitoring and event detection 362 may control sensor selection module 366 to select a different or additional acoustical sensor 351a through 351n to be coupled to sense amplifiers 352a through 352n to acquire additional signal information for detecting or discriminating a respiratory or cardiac condition. For example, if a heart sound 358 or respiratory sound 356 changes in a way that indicates a serious pathological problem, an acoustical sensor located for detecting pathological respiratory sounds, such as crackles or wheezing, may be selected and coupled to narrow bandpass filters 354 via switch 353 and a respective sense amplifier 352a-352n.

A change in a monitored sound may be an increase or decrease in an amplitude, slope, frequency, or other feature of an acoustical signal, including a complete disappearance or appearance of a signal feature. Detecting a change in a monitored sound may include detecting a change in a pattern of the monitored sound, for example a rate change, change in actual or relative duration of the sound with respect to another event or sound, or the like.

Figure 6:
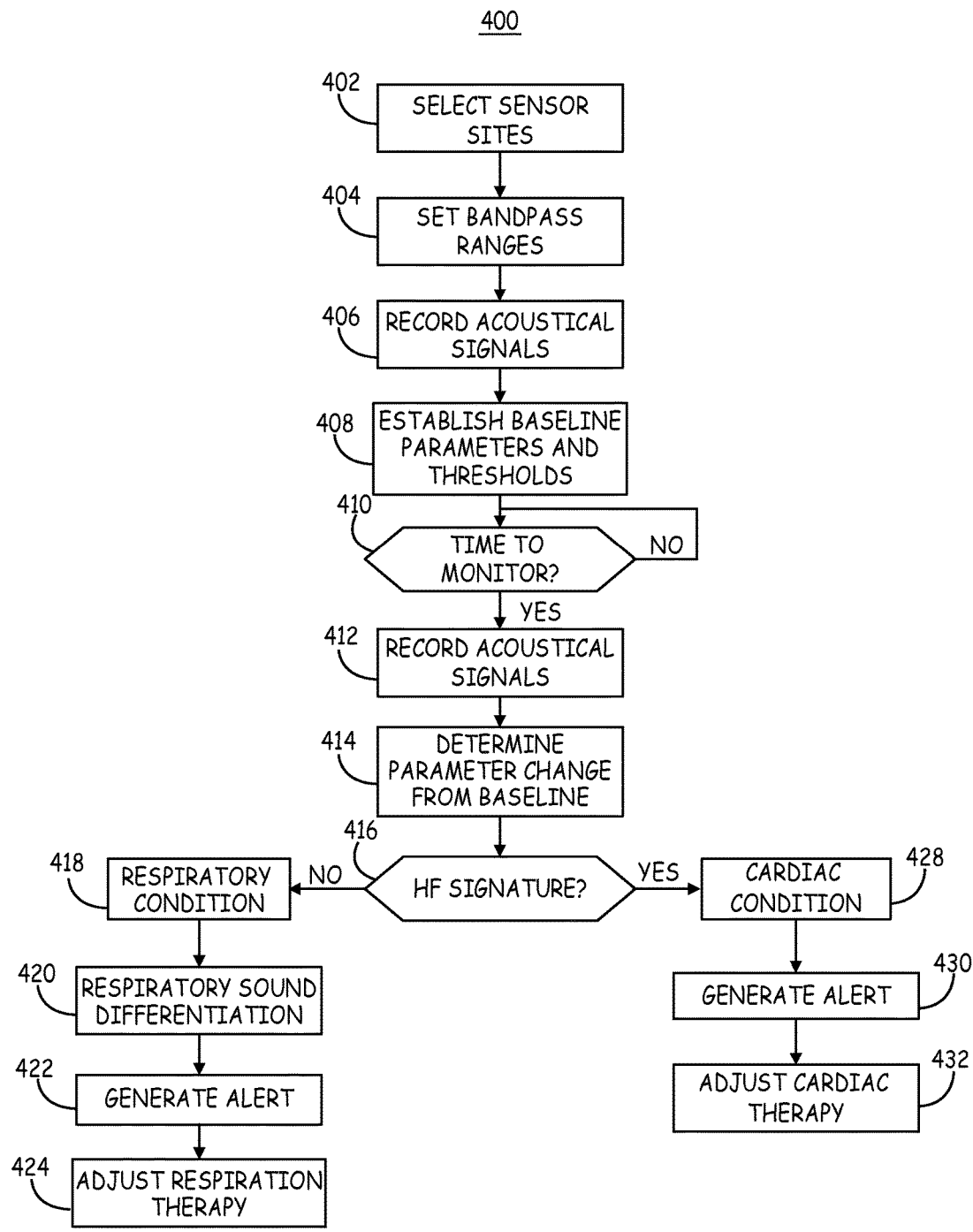
FIG. 6 is a flow chart of a method for detecting and discriminating respiratory and cardiac conditions using acoustical signals according to one embodiment.

FIG. 6 is a flow chart 400 of a method for detecting and discriminating respiratory and cardiac conditions using acoustical signals. Flow chart 400 and other flow charts presented herein are intended to illustrate the functional operation of the medical device, and should not be construed as reflective of a specific form of software, firmware or hardware necessary to practice the methods described. It is believed that the particular form of software, firmware, hardware or combination thereof will be determined primarily by the particular system architecture employed in the acoustical signal sensing system and by the particular sensing and therapy delivery methodologies employed. Providing software, firmware, or hardware to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 402, acoustical sensor sites are selected which allow differentiation between respiratory sounds and establish a good signal-to-noise ratio of respiratory sounds. Acoustical sensors may additionally be used to acquire heart sounds, though other physiological sensors may be used to acquire cardiac signals. More than one acoustical sensor may be used. Each sensor signal is acquired using a sampling rate and bandpass frequency for optimizing signal acquisition of a particular heart or respiratory sound obtained at a particular anatomical location. As such, bandpass filtering ranges are set at block 404 corresponding to each signal being acquired.

At block 406, acoustical signals are recorded. Baseline acoustical signal parameters are established at block 408. Establishing baseline parameter measurements may include measuring features such as signal amplitude, signal frequency content, time intervals, and signal derivatives. From these measurements various respiration metrics may be determined such as breathing rate and rhythm (i.e. pattern of inspiration and expiration duration during respiration cycles), breathing depth, e.g. based on an amplitude or peak-to-peak measurement, inspiratory and/or expiratory effort based on amplitude or frequency content, slope, inspiration duration, expiration duration, area under the signal during inspiration or during expiration, etc. Additionally the presence or absence of high frequency respiratory sounds such as wheezing, crackles or other pathological sounds may be established. Establishing baseline parameters may additionally include establishing cardiac metrics based on heart sounds or other cardiac signals.

In addition to establishing a patient's own baseline parameters, thresholds or other criteria for detecting events may be established at block 408. In one embodiment, a heart failure (HF) signature is established and used for detecting cardiac-related events. The heart failure signature is a combination of respiratory sound and cardiac signal metrics characteristic of congestive heart failure. A heart failure signature may be defined, for example, as including the presence of crackles as detected as a higher amplitude or higher frequency, short duration component of an acoustical signal, particularly of a signal acquired at a relatively inferior level corresponding to the alveoli and area of fluid accumulation as compared to a signal acquired relatively superior level along the trachea or bronchioles.

A heart failure signature may further include a breathless pattern evidenced by increased breathing rate and decreased breathing depth (e.g. short respiration cycle length and decreased signal amplitude during inspiration). The heart failure signature may additionally include heart sound-related criteria, such as an increase in the QRS-S1 interval, decreased S1 amplitude, and/or the appearance of the S3 sound.

At block 410, a decision is made whether to analyze acoustical signals for detecting a respiratory or cardiac condition. As described previously, an acoustical signal may be monitored continuously or periodically and a change in the acoustical signal may trigger the acquisition and analysis of one or more additional acoustical signals, at different anatomical locations and/or in different frequency bands of a given acoustical signal. Alternatively, another signal may be monitored, such as cardiac EGM, ECG, or another physiological signal and trigger the analysis of acoustical signals based on an event or change detected in the monitored signal.

It is recognized that the selection of sensor sites from which signals are acquired (block 402) and/or the frequency bands used to filter acoustical signals selected at block 404 may be adjusted and updated throughout the monitoring protocol in response to analysis of one or more acoustical or other physiological signals as described in conjunction with FIG. 5. At block 412, acoustical signals are selected and recorded. The signal parameters are measured at block 414 for comparison to baseline measurements.

The relative changes in measurements of the respiratory sounds from the established baseline measurements are determined. Additionally, relative changes in heart sound parameters may be measured. The measured changes are compared to event detection criteria at block 416. In one embodiment, the relative changes are compared to the established HF signature. With reference to the example given above, if the presence of a respiratory sound corresponding to a "crackle" is detected, a breathless breathing pattern is detected, and defined changes in heart sounds including at least one of a decreased S1 amplitude, increased QRS-S1 interval duration, or presence of S3 are detected, the HF signature is detected at block 416.

If the heart failure signature is detected, the change in acoustical signals is detected as a cardiac condition at block 428. A patient or physician alert may be generated at block 430 so that the patient will seek medical attention and a clinician can intervene early to reduce the likelihood of hospitalization. If the patient is implanted with a therapy delivery device, a cardiac therapy may be adjusted at block 432. Therapy adjustment may include turning on or off a therapy or adjusting a therapy control parameter. For example, in the IMD shown in FIG. 1, the IMD 10 may be configured to automatically adjust cardiac resynchronization therapy (CRT) control parameters in response to detecting a HF signature based at least in part on respiratory sounds. It is further contemplated that the adjustment of an automatic therapy may be performed in a closed loop manner with the respiratory sounds being analyzed after therapy adjustment to determine if the therapy is having a beneficial effect in reversing the HF signature conditions.

If the HF signature is not detected at block 416, the change in respiratory acoustical signals is determined to be caused by a respiratory condition rather than a cardiac condition at block 418. At block 420, additional analysis of respiratory sounds may be performed to differentiate between respiratory conditions or to confirm detection of a respiratory condition. For example, respiratory sound parameters may be examined for changes that correspond to asthma, central sleep apnea, obstructive sleep apnea, sudden breathing cessation due to injury or other causes or other breathing disorders.

An alert is generated at block 422 to alert the patient or clinician of the detected respiratory condition. If the acoustical sensing device is implemented in a medical device system capable of delivering a respiration therapy, the therapy may be turned on or adjusted at block 424.

The method shown by flow chart 400 is beneficial, for example, in a heart failure patient also suffering from a respiratory disorder, such as asthma. Early detection of worsening HF or an asthmatic episode allows the patient and/or a clinician to intervene early and take appropriate action for treating the properly identified underlying cause, whether it be HF or asthma. The patient may begin to experience difficulty in breathing or shortness of breath, for example, and have difficulty determining with certainty whether the change is due to congestive heart failure or an asthmatic episode. If a HF signature is not detected, changes in the respiratory sounds are determined to be caused by a respiratory condition. A patient alert may enable the patient to use a prescribed asthma medication. On the other hand if the HF signature is detected, a patient alert may prevent the patient from using unnecessary asthma medication and enable an implanted device to automatically adjust a HF therapy such as CRT to improve the patient's condition (or enable a clinician to intervene). Furthermore, it is recognized that the respiratory condition or the HF condition may be detected earlier than the patient would perceive the changing condition, thus allowing earlier intervention to take place, potentially precluding a more severe respiratory condition or cardiac condition.

Figure 7:
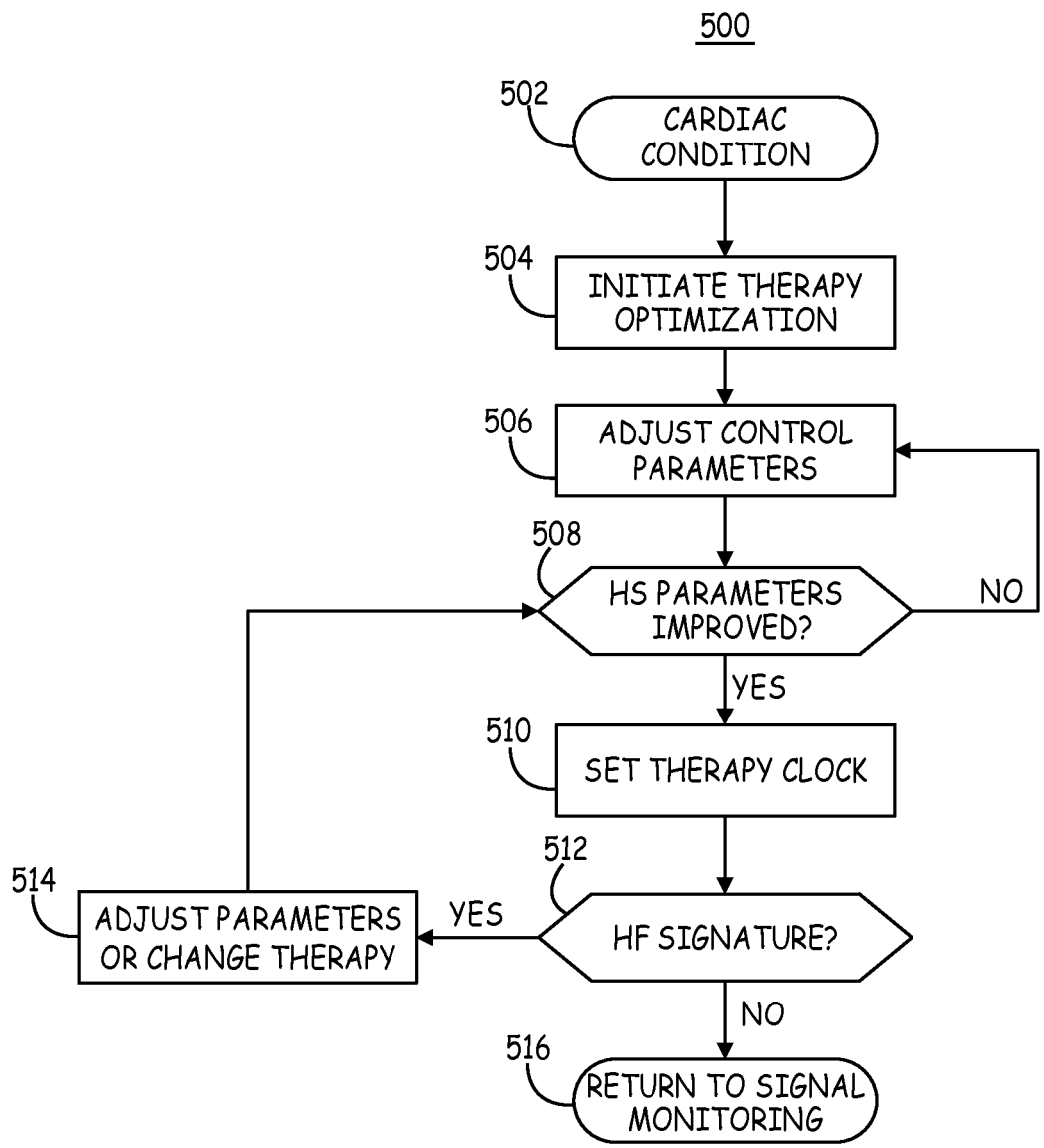
FIG. 7 is a flow chart of a method for closed-loop control of cardiac therapy using respiratory sounds according to one embodiment.

FIG. 7 is a flow chart 500 of a method for closed-loop control of cardiac therapy using respiratory sounds. When a cardiac condition is detected, as indicated at block 502, based on detection of a HF signature as described in conjunction with FIG. 6, a cardiac therapy optimization procedure is initiated at block 504. A cardiac therapy may be CRT, cardiac contraction modulation (CCM) in which electrical pulses are delivered to the myocardium to increase ventricular contractility, neurostimulation, a drug therapy, or any combination thereof.

A therapy optimization procedure initiated at block 504 typically includes adjusting one or more therapy control parameters until an improvement in a hemodynamic measurement or hemodynamic surrogate is achieved. In some embodiments, optimization of the therapy control parameters may include physician intervention, e.g. using Doppler echocardiography or other clinical techniques. In other embodiments, optimization of the therapy control parameters involves automatic adjustment of control parameters at block 506 until optimized parameter setting(s) are identified.

Therapy control parameters may be adjusted at block 506 until the acoustic parameters included in the HF signature are improved as determined at block 508. In an illustrative example, CRT optimization is initiated at block 504. CRT control parameters are adjusted at block 506 until the heart sound parameters included in the established HF signature criteria are improved. With reference to the example of a HF signature metric given above, the CRT control parameter(s) are adjusted until an increase in S1 amplitude and an increase in the QRS-S1 time interval are detected. Additionally or alternatively, optimized control parameters may be identified when S3 is decreased or disappears.

CRT control parameters may include atrial-ventricular (AV) interval, interventricular (VV) interval, and pacing site. Other examples of therapy control parameters that may be adjusted at block 506 include pulse amplitude, pulse shape, pulse rate, and pulse frequency. The therapy control parameters that are optimized will depend on the particular therapy being delivered.

Once an improvement in at least one heart sound parameter included in the HF signature is achieved, as determined at decision block 508, a therapy clock is set at block 510 to control delivery of the optimized therapy for a predetermined time interval. A therapy delivery time interval is typically at least one hour, and more typically at least 24 hours, but may be longer or shorter intervals depending on the type of therapy being delivered and an expected therapy response time.

After the therapy clock has expired, acoustic signals are monitored at block 512 to determine if the HF signature is still present. In particular, respiratory sounds are analyzed to determine if the respiratory sound parameters have reversed such that the HF signature is no longer detected. For example, high frequency sound parameters measuring the presence of crackles and respiration sound parameters measuring the presence of breathlessness are derived and examined. If the HF signature is no longer met as determined at block 512, the method returns to a signal monitoring mode at block 516, e.g. to block 410 of FIG. 6, and the adjusted therapy is maintained.

If the HF signature is still present, therapy control parameter(s) may be adjusted further at block 514 until the HF signature is no longer present. Alternatively, the therapy may be changed at block 514. A second therapy may be added to the existing therapy or the existing therapy may be discontinued and a new therapy initiated and optimized until the HF signature is no longer detected. For example, if CRT is initially optimized but the HF signature is still present after expiration of a therapy delivery time interval, CCM may be initiated at block 514 in addition to or instead of CRT. In other embodiments, a drug therapy may be titrated until a HF signature is no longer detected. In this way, the therapy is not only optimized based on relatively short term changes in hemodynamic-related HS signals but also optimized based on the relatively longer term changes in respiratory sounds that reflect the HF condition.

Figure 8:
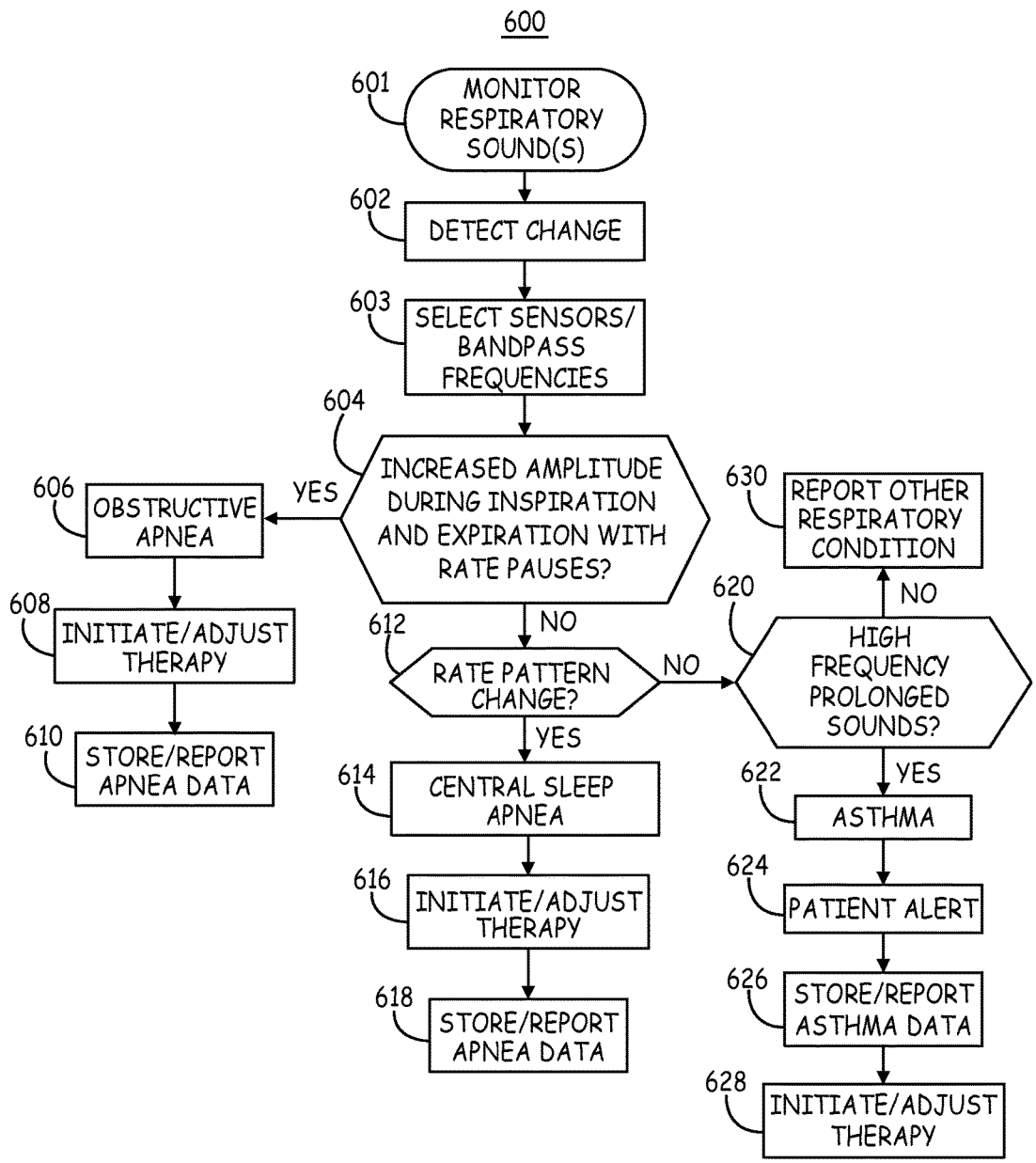
FIG. 8 is a flow chart of a method for discriminating between respiratory conditions using acoustical signals according to one embodiment.

FIG. 8 is a flow chart 600 of a method for discriminating between respiratory conditions using respiratory sounds. The method shown by flow chart 600 is initiated when respiratory sounds (block 601) are monitored and a change in an established baseline is detected at block 602. It is recognized that some respiratory changes may be normal physiological changes, e.g. fast breathing during activity. As such, detecting a respiratory change at block 602 that triggers acoustic signal analysis for discriminating respiratory conditions may require additional criteria based on other sensors and/or more than one acoustical signal. For example, if a change in breath pattern (i.e. rate and/or depth) is detected, a time of day clock, patient activity sensor, posture sensor, heart rate or other physiological signal may be examined to determine if the respiration sound change is associated with a normal physiological response to patient activity, a change in acoustical signals due to a posture change, or other non-pathological change. It is further contemplated, that whenever a respiration sound change is detected that is not determined to be a suspected pathological condition, i.e. determined to be a normal physiological respiration change, the acoustical signals may be used to update baseline respiration measurements for a particular time of day, patient activity or patient posture.

With reference to the method of FIG. 6, the respiratory condition discrimination methods shown by flow chart 600 may be initiated when a HF signature is not detected and a change in monitored acoustical signals is determined to be a respiratory condition (block 418). Alternatively, the method shown by flow chart 600 could be implemented independently of detecting cardiac related conditions such that acoustical signals are monitored and detection of a change initiates respiratory condition discrimination techniques.

In response to detecting a change in a monitored acoustical sound, acoustical sensors and/or bandpass frequencies are selected at block 603 to begin monitoring different amplitude, time interval patterns, and/or frequency content of a monitored signal and/or monitoring additional respiratory sounds from different sensing locations. The additional acoustical information is used for discriminating between different respiratory conditions. While blocks in flow chart 600 are shown in a particular order, it is recognized that operations associated with the flow chart blocks may be performed in a different order than that shown in flow chart 600 and in other flow charts presented herein. Furthermore, some blocks may be added or omitted in other embodiments.

It is further noted that one or more respiratory condition signatures of acoustical signals may be established, similarly to establishing a HF signature as described previously herein. While not shown explicitly in FIG. 8, it is contemplated that one or more respiratory condition signatures are established and stored in memory to enable detection criteria to be applied by the processor at the various decision blocks 604, 612, and 620 described below. A respiratory condition signature may include one or more amplitude, time interval, frequency or other acoustic signal parameter requirements. Signal parameters may be derived from one or more bandpass signals and/or one or more signals from different anatomical locations. The established signatures will be respiratory condition-dependent and may require no change in some frequencies or time-based portions of a signal while changes in other frequencies or time-based portions of a signal may be required to present a change to verify detection of a particular respiratory condition.

For example, at decision block 604, acoustic signal parameters are analyzed to determine if a respiratory sound presents an increased amplitude during an inspiration phase and during an expiration phase and if breathing rate pauses occur. Such changes are indicative of obstructive sleep apnea, as detected at block 606 in response to an affirmative result at block 604. In particular, the acoustic signal sensed near the trachea or upper airways is analyzed to determine if the amplitude content of the signal is increased during an inspiration phase and during an expiration phase.

Respiration phases may be identified, for example, based on zero-crossings, inflection points, slope changes, threshold crossings or other methods. These methods for detecting respiration phases may also be used to detect a respiration rate using a fiducial point identified during the respiration cycle. If a long respiration pause is detected, for example greater than some percentage of an average respiration cycle length, this result in combination with increased inspiration and expiration sounds supports an obstructive sleep apnea detection at block 606.

It is recognized that respiratory discrimination methods shown in FIG. 8 may include the use of other signals to confirm the logic of a respiratory condition detection. For example, a time of day clock, patient activity, patient posture, heart rate or other metrics may be used in combination with respiratory sounds for detecting respiratory conditions. An obstructive apnea condition would be expected during a period of rest and non-standing position for example.

If obstructive apnea is detected and the detection algorithm is implemented in conjunction with a device capable of delivering an apnea therapy, a sleep apnea therapy may be adjusted or initiated automatically at block 608. For example, electrical stimulation of the muscles of the upper airway or vagal nerve stimulation may be initiated or adjusted. Parameters controlling stimulation pulse delivery in either therapy may be adjusted, such as pulse amplitude, pulse width, pulse frequency, pulse number, pulse train rate, pulse shape, stimulation site, etc. It is to be understood that the therapy delivery may be controlled in a closed-loop manner using the respiratory sounds as feedback until the detected condition is alleviated. As such, monitoring of the selected respiratory sounds may continue periodically or continuously during the therapy delivery.

At block 610, data corresponding to the apnea detection may be stored and/or included in a report transmitted to an external device for display to a clinician. Alternatively, the detection may cause a patient or clinician alert to be generated.

If the criteria for detecting obstructive apnea are not satisfied at block 604, criteria for detecting central sleep apnea may be applied to acoustic signal parameters at block 612. In particular, if an increased amplitude of respiration sounds during inspiration and expiration was not detected at block 604, but a rate pattern change exists, as determined at block 612, central sleep apnea is detected at block 614. A rate pattern change is detected when the breathing rate presents episodes of faster and slower breathing. In addition to rate pattern changes, verification of no increase in inspiratory or expiratory effort may be made, e.g. based on frequency content of the acoustical signals. An increase in inspiratory or expiratory effort would be indicative of other types of respiratory conditions, not central sleep apnea.

If a rate pattern change is detected, such as a brief long pause between two breaths or an irregular breath rate, central sleep apnea is detected at block 614. If the detection algorithm is implemented in conjunction with a device capable of delivering a central sleep apnea therapy, the therapy may be initiated or adjusted at block 616. A central sleep apnea therapy may include phrenic nerve or spinal cord stimulation. The therapy control parameters controlling stimulation pulse delivery may be adjusted under closed-loop feedback using the respiratory sounds as generally described above. At block 618, a patient or clinician alert or report may be generated and/or the apnea data may be stored for later transmission and display to a clinician.

If a rate pattern change is not detected at block 612, other respiratory sound patterns or features may be examined at block 620. For example, if a high frequency prolonged sound is detected at block 620, asthma is detected at block 622. If a high-frequency passband signal is found to increase in power, for example, wheezing associated with asthma or an asthma-like condition such as chronic obstructive respiratory disease (COPD) may be present.

A high-pitched wheezing associated with asthma or an asthma-like condition may be distinguished from high-pitched "crackles" associated with heart failure based on the duration of the sound. Crackles will tend to be short, e.g. less than 100 ms, and irregular while wheezing associated with asthma will have a longer duration, e.g., greater than 100 ms, and present a more regular cyclical pattern with the respiration cycle. Wheezing will typically be detected primarily during expiration whereas crackles occur during or at end-inspiration. As such, a sound duration threshold may be applied to the high frequency signal to detect wheezing sounds and differentiate a wheeze from a crackle. Furthermore, the primary frequency component will tend to be different between crackles and wheezing thus a frequency threshold and/or a duration threshold may be applied in respiration sound signatures which may further include detecting the particular sound characteristics during a predefined time window of the respiration cycle, e.g. inspiration vs. expiration phase.

If high frequency prolonged sounds are detected at block 620, asthma is detected at block 622. A patient alert may be delivered at block 624 to notify the patient that an asthma medication is needed. Additionally, data may be stored at block 626 for later transmission or report generation for display to a clinician on an external device or computer. If a device-delivered therapy is available, such as a drug pump delivering an asthma medication or electrical stimulation to cause airway relaxation, a therapy may be delivered or adjusted at block 628. As indicated previously, any therapy delivered to alleviate a respiratory condition may be delivered using closed-loop feedback control based on respiratory sounds.

If prolonged high frequency sounds are not detected at block 620, an indiscriminate detection of a respiratory condition may be made at block 630. Other examples of respiratory conditions that may be detected, discriminately or indiscriminately, may include chest injury, inflammation or pleurisy which may cause sudden brief breathing cessation due to pain or inflammation.

A respiratory sound signature may also be defined for discriminating chronic obstructive pulmonary disease (COPD) which may be characterized by wheezes, respiratory changes after a deep breath or cough, and whether wheezes are monophonic (suggesting obstruction of one airway) or polyphonic (suggesting generalized obstruction of airways).

Figure 9:
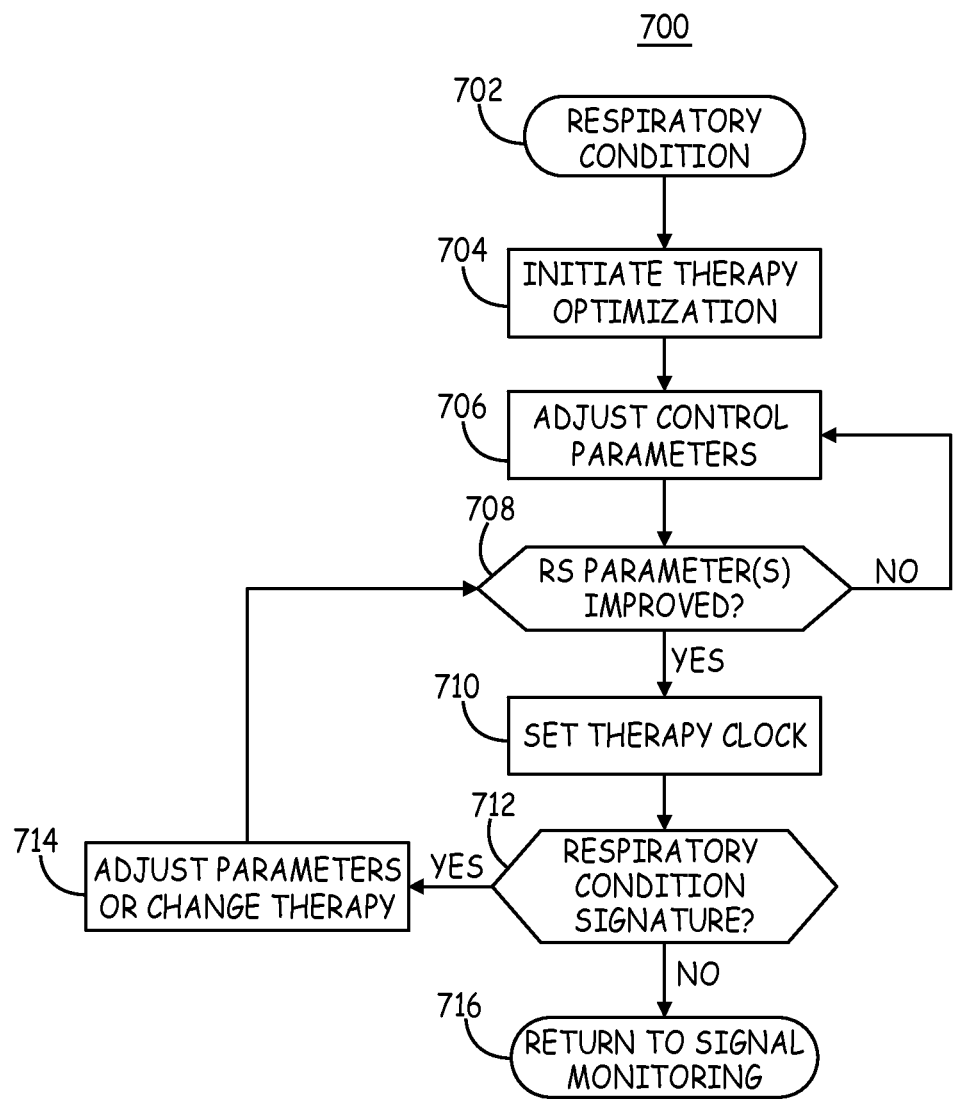
FIG. 9 is a flow chart of a method for closed-loop control of a respiration therapy using respiratory sounds according to one embodiment.

FIG. 9 is a flow chart 700 of a method for closed-loop control of a respiration therapy using respiratory sounds. When a respiratory condition is detected, as indicated at block 702, based on detection of a respiratory condition signature as described in conjunction with FIG. 8, a respiration therapy optimization procedure is initiated at block 704. A therapy may be an electrical stimulation therapy, such as phrenic nerve stimulation, stimulation of the upper airway muscles, diaphragm stimulation, stimulation of the vagus nerve, stimulation of the central nervous system, or a drug therapy delivered by a drug pump or any combination thereof.

A therapy optimization procedure initiated at block 704 typically includes adjusting one or more therapy control parameters until an improvement in a respiratory sound measurement is achieved. In some embodiments, optimization of the therapy control parameters may include physician intervention, e.g. using ventilation measurements or other clinical techniques. In other embodiments, optimization of the therapy control parameters involves automatic adjustment of control parameters at block 706 until optimized parameter setting(s) are identified.

Therapy control parameters may be adjusted at block 706 until the respiratory sound parameters included in the respiratory condition signature that was met causing a respiratory condition detection are improved as determined at block 708. In an illustrative example, an electrical stimulation therapy optimization is initiated at block 704. Stimulation control parameters are adjusted at block 706 until at least one respiratory sound (RS) parameter included in the established respiratory condition signature criteria is improved. For example, restoration of a regular rate or depth of respiration may be established. With reference to the example of a respiratory condition signature metric given above for obstructive sleep apnea, the therapy control parameter may be adjusted until a threshold decrease in the inspiratory and expiratory sound amplitudes is achieved.

Therapy control parameters may include any of those mentioned previously, such as pulse rate, pulse amplitude, pulse width, pulse number, frequency or duration when pulse trains are used, stimulation site, and so on. If a drug therapy is delivered, titration of the drug dosage may be controlled. The therapy control parameters that are optimized will depend on the particular therapy being delivered. It is understood that the therapy may be delivered at an adjusted control parameter for an interval of time to allow any delay in therapeutic benefit to take place, such as a delay associated with the pharmacokinetic properties of a drug being delivered.

Once an improvement in at least one respiratory sound parameter included in the respiratory condition signature is achieved, a therapy clock is set at block 710 to control delivery of the optimized therapy for a predetermined time interval. A therapy delivery time interval is typically at least one hour, and more typically at least 24 hours, but may be longer or shorter intervals depending on the type of therapy being delivered and an expected therapy response time. In the case of a respiration therapy, the therapy time interval may be one minute, several minutes or another interval less than one hour to ensure that respiration is properly maintained to ventilate the patient.

After the therapy clock has expired, acoustic signals are monitored at block 712 to determine if the detected respiratory condition signature is still present. In particular, respiratory sounds are analyzed to determine if the respiratory sound parameter changes have reversed such that the respiratory condition signature is no longer detected. Parameters corresponding to the presence of rate or inspiration/expiration pattern changes, loudness or pitch changes and presence of high frequency sounds are derived and examined according to the respiratory condition signature. If the respiratory condition signature is no longer detected, the method returns to a signal monitoring mode at block 716, e.g. to block 410 of FIG. 6, and the adjusted therapy is maintained.

If the respiratory condition signature is still present, therapy control parameter(s) may be adjusted further at block 714 until the signature is no longer detected. Alternatively, the therapy may be changed at block 714. A second therapy may be added to the existing therapy or the existing therapy may be discontinued and a new therapy initiated and optimized until the respiratory condition signature is no longer detected.

Thus, a medical device system and associated methods have been presented in the foregoing description with reference to specific embodiments. It is appreciated that various modifications to the referenced embodiments may be made without departing from the scope of the disclosure as set forth in the following claims.

The invention claimed is:

1. A medical device system, comprising:
a first acoustic transducer;
a sensing module coupled to the first acoustic transducer and configured to acquire a first signal and a second signal, at least the second signal being an acoustical signal received from the first acoustic transducer and comprising a respiratory sound of air flow through at least a portion of a tracheobronchial tree or lungs of a patient; and
a processor configured to receive the first signal, control the sensing module to acquire the second acoustical signal in response to a change in the first signal, determine a metric of the respiratory sound from the second signal, discriminate between a cardiac condition and a respiratory condition as a cause of the change in the first signal in response to the metric, and control a therapy delivery module to adjust a therapy in response to discriminating the condition.

2. The system of claim 1, further comprising a second acoustic transducer,
the sensing module configured to acquire the first signal from the second acoustic transducer, the first signal corresponding to a first anatomical location and the second signal corresponding to a second anatomical location different than the first.

3. The system of claim 2, wherein one of the first and second acoustic transducers is anatomically positioned superiorly along a craniocaudal axis with respect to the other of the first and second acoustic transducers,
the processor configured to detect the respiratory condition in response to a change in the respective signal of the one of the first and second acoustic transducers positioned superiorly.

4. The system of claim 1, wherein the sensing module comprises a plurality of bandpass filters and acquires the second acoustical signal by enabling a bandpass filter.

5. The system of claim 4, wherein a first one of the plurality of bandpass filters is centered on a frequency corresponding to the respiratory sound and the first signal is acquired by the sensing module by setting a second one of the plurality of bandpass filters to a frequency corresponding to a heart sound.

6. The system of claim 4, wherein one of the plurality of bandpass filters is centered on a frequency corresponding to a pathological respiratory sound and provides a pathological respiratory sound signal.

7. The system of claim 6, wherein the processor is configured to detect a respiratory condition in response to the pathological respiratory sound signal having a respiratory sound duration greater than a predetermined threshold.

8. The system of claim 1, further comprising the therapy delivery module.

9. The system of claim 1, wherein the processor is further configured to adjust a therapy control parameter until a change in the second acoustical signal is no longer detected.

10. The system of claim 1, wherein the processor is configured to adjust the therapy until the first signal no longer meets a first detection condition, set a therapy timer, upon expiration of the therapy timer determine if the second acoustical signal meets a second detection condition, and adjust the therapy in response to the second acoustical signal still meeting the second detection condition.

11. The system of claim 1, wherein the respiratory sound comprises one of a tracheal sound, a bronchial sound, a bronchovesicular sound, and a vesicular sound, the processor further configured to determine a baseline metric of the respiratory sound from the second acoustical signal prior to determining the change in the first signal, and discriminate between the cardiac condition and the respiratory condition by comparing the metric of the respiratory sound to the baseline metric.

12. A medical device system, comprising:
a first acoustic transducer;
a sensing module coupled to the first acoustic transducer and configured to acquire a first signal and a second signal, at least the second signal being an acoustical signal received from the first acoustic transducer and comprising a respiratory sound of air flow through at least a portion of a tracheobronchial tree or lungs of a patient; and
a processor configured to receive the first signal, control the sensing module to acquire the second acoustical signal in response to a change in the first signal, determine a metric of the respiratory sound from the second signal, and discriminate between a cardiac condition and a respiratory condition as a cause of the change in the first signal in response to the metric wherein:
the sensing module comprises a plurality of bandpass filters;
the processor is further configured to:
control the sensing module to acquire the first signal from the first acoustic transducer by selecting a first bandpass filter of the plurality of bandpass filters;
acquire the second acoustical signal in response to the change in the first signal by controlling the sensing module to apply a second bandpass filter different than the first bandpass filter to obtain first respiratory signals produced at a first anatomical location;
control the sensing module to acquire a third acoustical signal in response to the change in the first signal by controlling the sensing module to apply a third bandpass filter different than the first and second bandpass filters to obtain second respiratory signals produced at a second anatomical location different than the first anatomical location;
discriminate between the cardiac condition and the respiratory condition as the cause of the change in the first signal based on the first respiratory signals and the second respiratory signals; and
control a therapy delivery module to adjust a therapy in response to discriminating the condition.

13. A method, comprising:
sensing a first signal by a sensing module of a medical device;
determining a change in the first signal by a processor of the medical device;
sensing a second signal from a first acoustic transducer coupled to the sensing module in response to the determined change in the first signal, the second signal comprising a respiratory sound of air flow through at least a portion of a tracheobronchial tree or lungs of a patient;
determining a metric of the respiratory sound from the second signal; and
determining a cause of the change in the first signal by the processor of the medical device by discriminating, in response to the metric, between a cardiac condition and a respiratory condition as the cause of the determined change in the first signal; and
delivering a therapy in response to discriminating the condition.

14. The method of claim 13, wherein the first signal is sensed from a second acoustic transducer, the first signal corresponding to a first anatomical location and the second signal corresponding to a second anatomical location different than the first.

15. The method of claim 14, wherein one of the first acoustic transducer and the second acoustic transducer is anatomically positioned superiorly along a craniocaudal axis with respect to the other of the first acoustical transducer and the second acoustical transducer, and further comprising detecting the respiratory condition in response to a change in the respective signal of the one of the first and second acoustic transducers positioned superiorly.

16. The method of claim 13, wherein sensing the second acoustical signal comprises activating one of a plurality of bandpass filters.

17. The method of claim 16, wherein:
sensing the second acoustical signal comprises selecting one of a first one of the plurality of bandpass filters centered on a frequency corresponding to the respiratory sound, and
sensing the first signal by the sensing module comprises setting a second one of the plurality of bandpass filters centered on a frequency corresponding to a heart sound.

18. The method of claim 16, wherein acquiring the second acoustical signal comprises selecting one of the plurality of bandpass filters centered on a frequency corresponding to a pathological respiratory sound.

19. The method of claim 18, further comprising detecting a respiratory condition in response to the pathological respiratory sound signal having a respiratory sound duration greater than a predetermined threshold.

20. The method of claim 13, further comprising adjusting a therapy control parameter until a change in the second acoustical signal is no longer detected.

21. The system of claim 13, further comprising:
adjusting the therapy until the first signal no longer meets a first detection condition;
setting a therapy timer, upon expiration of the therapy timer determining if the second acoustical signal meets a second detection condition; and
adjusting the therapy in response to the second acoustical signal still meeting the second detection condition.

22. A computer-readable medium storing instructions which cause a medical device system to perform a method comprising:
sensing a first signal;
determining a change in the first signal;

sensing a second signal from an acoustic transducer in response to the determined change in the first signal, the second signal comprising a respiratory sound of air flow through at least a portion of a tracheobronchial tree or lungs of a patient;

determining a metric of the respiratory sound from the second signal;

discriminating, in response to the metric, between a cardiac condition and a respiratory condition as a cause of the determined change in the first signal; and delivering a therapy in response to discriminating the condition.

\* \* \* \* \*

UNITED STATES PATENT AND TRADEMARK OFFICE
CERTIFICATE OF CORRECTION

| | |
|---|---|
| PATENT NO. | : 10,595,813 B2 |
| APPLICATION NO. | : 13/456346 |
| DATED | : March 24, 2020 |
| INVENTOR(S) | : Song et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2073 days.

Signed and Sealed this
Sixth Day of December, 2022

Katherine Kelly Vidal
*Director of the United States Patent and Trademark Office*